(12) United States Patent
Bailey

(10) Patent No.: US 7,243,676 B2
(45) Date of Patent: Jul. 17, 2007

(54) COMBINATION UMBRELLA AND INVERTED BI-DIRECTIONAL VALVE

(75) Inventor: James Christopher Bailey, Yellow Springs, OH (US)

(73) Assignee: Vernay Laboratories, Inc., Yellow Springs, OH (US)

( * ) Notice: Subject to any disclaimer, the term of this patent is extended or adjusted under 35 U.S.C. 154(b) by 360 days.

(21) Appl. No.: 10/848,782

(22) Filed: May 19, 2004

(65) Prior Publication Data

US 2005/0257837 A1 Nov. 24, 2005

(51) Int. Cl.
*F16K 15/14* (2006.01)
(52) U.S. Cl. .............................. 137/512.15; 137/493.1; 137/493.9; 137/512.3
(58) Field of Classification Search .......... 137/512–15, 137/512.4, 512.3, 493.1, 493.9; 222/491, 222/494
See application file for complete search history.

(56) References Cited

U.S. PATENT DOCUMENTS

| | | | |
|---|---|---|---|
| 3,036,592 A | 5/1962 | Lips | |
| 3,043,404 A | 7/1962 | Peras | |
| 3,159,176 A | 12/1964 | Russell et al. | |
| 3,179,122 A | 4/1965 | Wasdell | |
| 3,941,149 A | 3/1976 | Mittleman | |
| 4,077,429 A * | 3/1978 | Kimball | 137/588 |
| 4,084,606 A | 4/1978 | Mittleman | |
| 4,434,810 A | 3/1984 | Atkinson | |
| 4,513,891 A * | 4/1985 | Hain et al. | 222/213 |
| 4,728,006 A | 3/1988 | Drobish et al. | |
| 5,010,925 A | 4/1991 | Atkinson et al. | |
| 5,325,885 A | 7/1994 | Ivan et al. | |
| 5,472,122 A | 12/1995 | Appleby | |
| 5,601,112 A | 2/1997 | Sekiya et al. | |
| 5,989,469 A | 11/1999 | Dirr | |
| 6,092,551 A | 7/2000 | Bennett | |
| 6,145,707 A | 11/2000 | Baudin | |
| 6,206,058 B1 | 3/2001 | Nagel et al. | |
| 6,230,940 B1 | 5/2001 | Manning et al. | |
| 6,283,147 B1 | 9/2001 | Rosseel | |
| 6,427,874 B2 | 8/2002 | Brown et al. | |
| 6,453,940 B1 | 9/2002 | Tipton et al. | |
| 6,468,435 B1 | 10/2002 | Hughes et al. | |
| 6,533,254 B1 | 3/2003 | Grifka et al. | |
| 6,616,016 B2 | 9/2003 | Hicks et al. | |
| 6,874,656 B2 | 4/2005 | Rohr et al. | |
| 6,874,999 B2 * | 4/2005 | Dai et al. | 417/413.2 |

FOREIGN PATENT DOCUMENTS

EP  1112710  7/2001
GB  1047315  11/1966

* cited by examiner

*Primary Examiner*—Ramesh Krishnamurthy
(74) *Attorney, Agent, or Firm*—Thompson Hine LLP

(57) ABSTRACT

A combination valve including a valve body having an inverted bi-directional valve portion and an umbrella portion is disclosed. In accordance with one aspect of the invention, a combination valve includes a valve body with a substantially cylindrical portion defining a flow path, a resilient umbrella valve portion extending annularly from the valve body and an inverted bi-directional valve portion provided in the flow path. The inverted bi-directional valve portion includes an interior surface, an exterior surface and at least one normally closed slit extending therebetween, wherein the exterior surface of the inverted bi-directional valve portion includes a generally concave curved portion when the slit is closed.

13 Claims, 4 Drawing Sheets

COMBINATION UMBRELLA AND INVERTED BI-DIRECTIONAL VALVE

BACKGROUND OF THE INVENTION

1. Field of the Invention

The present invention relates to combination fluid valves, and in particular to combination valves comprising an inverted bidirectional valve in combination with an umbrella valve capable of providing flow responsive to changes in pressure differential.

2. Description of the Related Art

Current combination fluid valves include those of the duckbill-umbrella variety. Duckbill-umbrella combination valves allow fluid (often air) into a container or pump chamber via the umbrella valve portion along a first flow path and allow a second fluid (often a liquid product) out of the container or pump chamber via the duckbill valve portion through a second flow path. However, the duckbill portion of the valve typically provides only limited prevention of flow in the dispensing direction and can leak under relatively low pressure differentials. For example, duckbill-umbrella combination valves can leak when used in conjunction with containers of liquid that are inverted during use.

It would be desirable to have a simple, unitary combination valve that is normally closed and allows fluid to be drawn out under differential pressure. A normally closed valve minimizes problems associated with spilling or dripping. It would also be desirable to have a combination valve that operates satisfactorily to prevent flow until a predetermined amount of pressure is achieved.

SUMMARY OF THE INVENTION

The present invention relates to a combination valve including a valve body having an inverted bi-directional valve portion and an umbrella portion. In accordance with one aspect of the invention a combination valve is disclosed including a valve body with a substantially cylindrical portion defining a flow path, a resilient umbrella valve portion extending annularly from the valve body and an inverted bi-directional valve portion provided in the flow path. The inverted bi-directional valve portion includes an interior surface, an exterior surface and at least one normally closed slit extending therebetween, wherein the exterior surface of the inverted bi-directional valve portion includes a generally concave curved portion when the slit is closed.

The present invention also provides a combination valve including an inverted bi-directional valve portion and a resilient umbrella portion integrally formed with a valve body. A normally closed slit in the inverted bi-directional valve is responsive at a first predetermined fluid pressure in a first direction to permit transfer of fluid in the first direction. The umbrella valve portion prevents transfer of fluid in a first direction and is responsive at a second predetermined fluid pressure in a second direction to permit fluid flow in the second direction.

In accordance with another aspect of the invention, the present invention provides a combination valve with a substantially cylindrical valve body having a central longitudinal axis and defining a flow path through the valve, a resilient umbrella portion extending annularly from the valve body and the valve body terminating at an end thereof in an inverted bi-directional valve portion. The inverted bi-directional valve portion in accordance with this aspect of the present invention has a curved contour about an axis of curvature extending substantially perpendicularly to and intersecting the central longitudinal axis. The inverted bidirectional valve portion has a linear contour perpendicular to the central longitudinal axis such that the inverted bidirectional valve portion is radially asymmetrical about the central longitudinal axis. The inverted bi-directional valve portion in its normal, relaxed state is characterized by a concave exterior surface and the inverted bi-directional valve portion flexes when subjected to a predetermined fluid pressure. The inverted bi-directional valve portion includes at least one slit that is normally closed when the valve is in its normal, relaxed state and opens after the valve is subjected to a predetermined fluid pressure and the inverted bi-directional valve flexes to open a flow path through the slit.

The valve body, umbrella portion and inverted bi-directional valve portions in accordance with certain aspects of the present invention are formed of one or more elastomeric materials such that the slit opens to permit flow through the inverted bi-directional valve portion in a first direction at or above a first predetermined pressure level and the umbrella valve portion flexibly responds to a second predetermined pressure level to permit flow in a second direction.

One advantage of the inventive combination fluid valve described herein is that the valve provides additional protection against leakage under low pressure conditions. The combination valve provides a delay in the onset of flow until there is sufficient pressure to flex the inverted bi-directional valve portion causing the slit to open. The inverted bi-directional valve causes standing fluid pressure below the opening threshold to maintain the slit in its closed position, until the applied pressure is increased sufficiently to cause the inverted bi-directional valve portion to flex and cause the slit to open thereby permitting flow through the open slit.

BRIEF DESCRIPTION OF THE DRAWINGS

The above mentioned and other features of this invention, and the manner of attaining them, will become more apparent and the invention itself will be better understood by reference to the following description of an embodiment of the invention taken in conjunction with the accompanying drawings, wherein.

Figure 1:
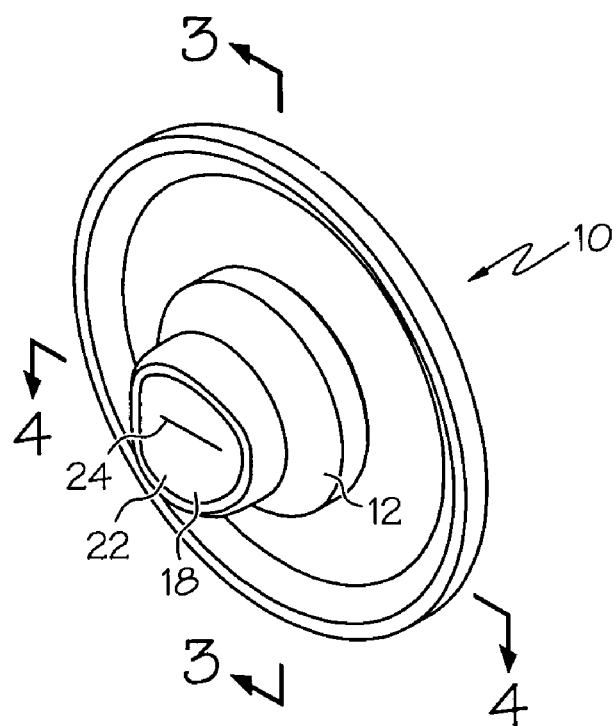
FIG. 1 is a perspective view of a valve in accordance with one aspect of the present invention showing the slit in its normally closed position.

Corresponding reference characters indicate corresponding parts throughout the several views. Although the drawings represent an embodiment of the present invention, the drawings are not necessarily to scale and certain features may be exaggerated in order to better illustrate and explain the present invention. The exemplification set out herein illustrates an embodiment of the invention, in one form, and such exemplification is not to be construed as limiting the scope of the invention in any manner.

DETAILED DESCRIPTION OF THE INVENTION

All documents cited are, in relevant part, incorporated herein by reference; the citation of any document is not to be construed as an admission that it is prior art with respect to the present invention.

The embodiment disclosed below is not intended to be exhaustive or limit the invention to the precise form disclosed in the following detailed description. Rather, the embodiment is described so that others skilled in the art may utilize its teachings, but represents only certain manifestations of the invention.

As used herein, the term "inverted bi-directional valve" refers to that portion of the combination valve having a structure similar to a conventional bi-directional valve except the flexing portion of the valve is inverted with respect to the substantially cylindrical portion. As a result, the inverted bi-directional valve described herein can be characterized as having a generally concave exterior surface, whereas a conventional bi-directional valve has a generally convex exterior surface. One example of a conventional bi-directional valve is disclosed in U.S. Pat. No. 4,434,810 to Atkinson.

With reference initially to FIGS. 1 through 4 of the drawings, it will be seen that a combination valve 10 in accordance with one aspect of the present invention includes a valve body portion 12 including a hollow, substantially cylindrical portion 14 defining a flow path 16 through the valve body 12. The valve body 12 terminates at one end in an inverted bi-directional valve portion 18 having an interior surface 20, an exterior surface 22 and a slit 24 extending therebetween. One of skill in the art will recognize that the slit membrane portion of the inverted bi-directional valve could be located anywhere along the length of the substantially cylindrical portion. The combination valve 10 also includes a resilient umbrella portion 26 extending annularly from an opposite end of the valve body 12. One of skill in the art will recognize that the umbrella valve portion 26 is not limited to being at one end of the valve body but could be extend from any part of the valve body 12. The valve 10 in accordance with particular embodiments of the present invention is of unitary molded construction made of a flexible, elastomeric material.

Figure 2:
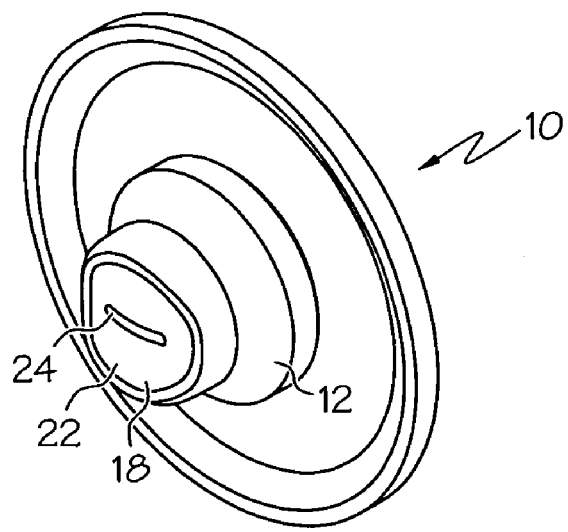
FIG. 2 is a view similar to FIG. 1, but showing the slit open for flow in a first direction.

In its normal, unstressed state, wherein the slit 24 is closed, the exterior surface 22 of the inverted bi-directional valve portion 18 is generally concave. When subjected to a sufficient predetermined fluid pressure, the inverted bi-directional valve portion 18 flexes and the slit 24 opens as seen in FIG. 2.

Figure 3:
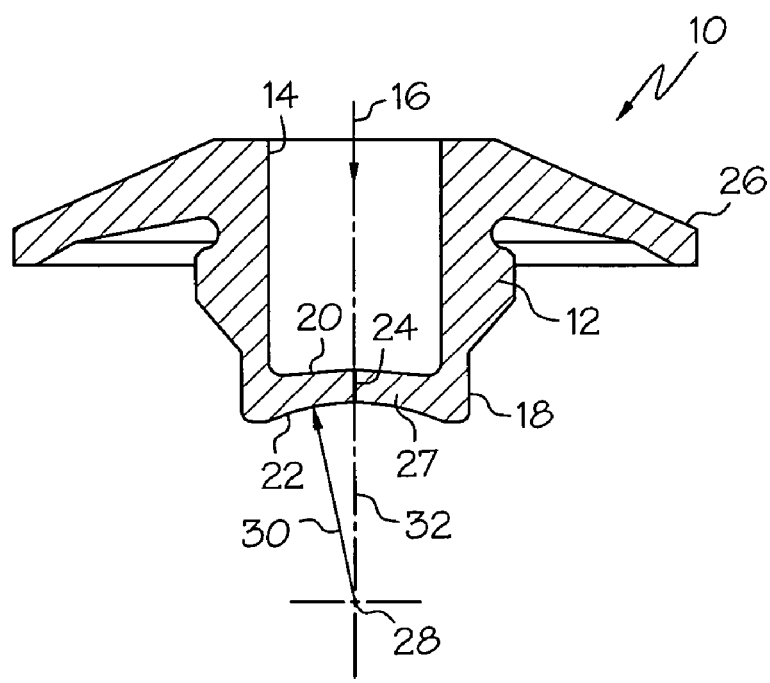
FIG. 3 is a cross-sectional view taken on line 3-3 of FIG. 1.

When viewed as in FIG. 3, the inverted bi-directional valve portion 18 has a curved contour 27 that curves about an axis of curvature 28 and preferably has an approximately constant radius of curvature 30. The axis of curvature 28 preferably lies on the central longitudinal axis 32 of the hollow, substantially cylindrical portion 14.

Figure 4:
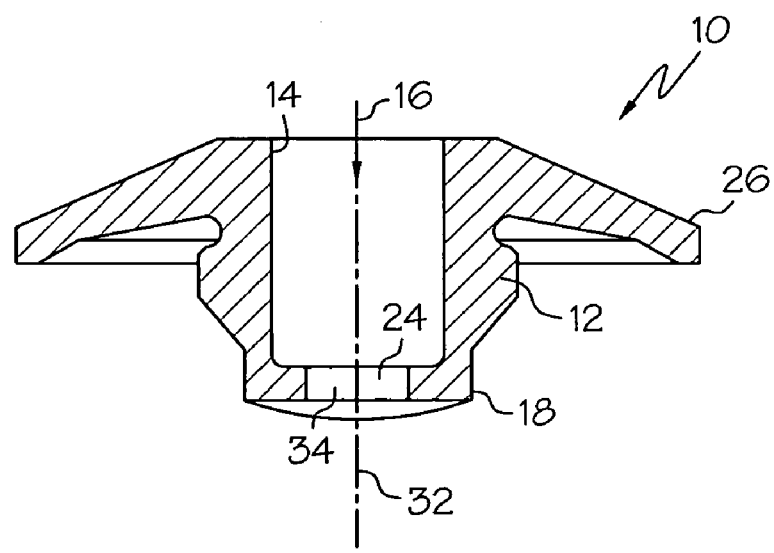
FIG. 4 is a partial cross-sectional view taken on line 4-4 of FIG. 1.

When viewed as in FIG. 4, the inverted bi-directional valve portion 18 has a linear contour 34 oriented substantially normal to the central longitudinal axis 32 and parallel to the axis of curvature 28. Thus, the inverted bi-directional valve portion presents a radially asymmetrical profile about the central longitudinal axis 32, having a curved contour 27 in the plane shown in FIG. 3, and a linear contour 34 in the plane shown in FIG. 4; the two planes preferably being normal to each other and containing the central longitudinal axis 32.

In accordance with a particular aspect of the present invention, slit 24 is formed in the inverted bi-directional valve portion 18 and extends along the linear contour 34. The slit 24 is normally closed and has a length less than the diameter of the valve body portion 12. In accordance with certain aspects of the present invention, the slit 24 intersects and is radially symmetric with respect to the central longitudinal axis 32.

Figure 5:
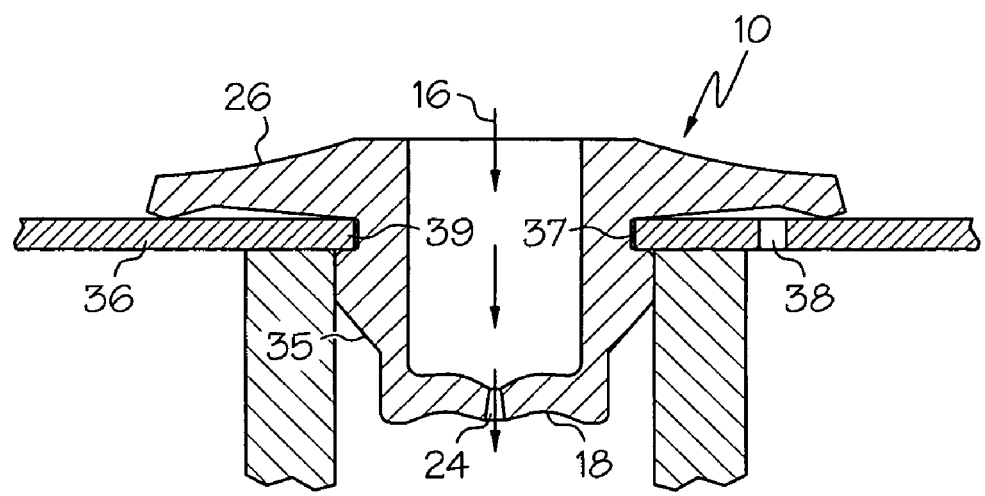
FIG. 5 is a cross-sectional view depicting the valve in conjunction with a container wall illustrating flow through the flow path of the valve body.
Figure 6:
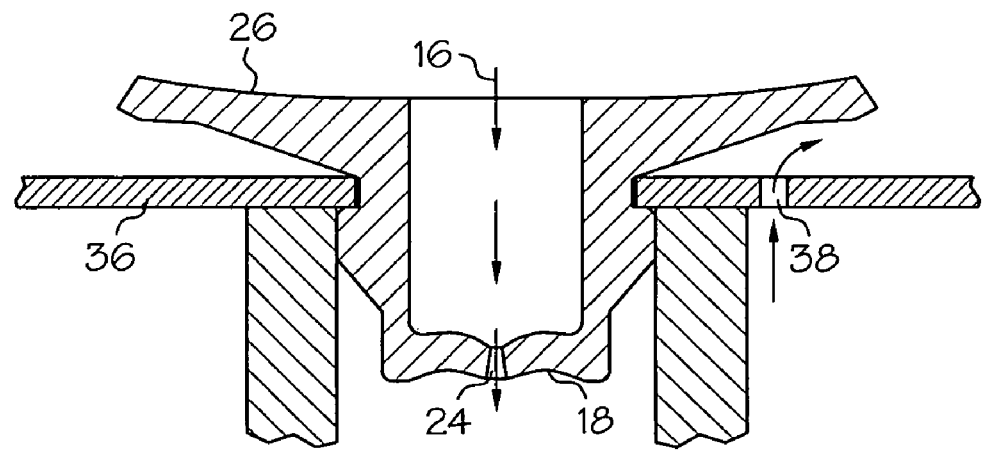
FIG. 6 is a cross-sectional view similar to FIG. 5 illustrating the operation of the umbrella valve to allow fluid flow in a second direction through a flow path around the periphery of the umbrella valve portion.

As shown in FIGS. 5 and 6, annular umbrella portion 26 extends from the valve body 12 and may seat against a fluid-restraining member such as a container wall 36 covering one or more fluid passageways 38 defined by container wall 36. In accordance with the valve 10 shown in FIGS. 5 and 6, the valve body 12 further includes a generally annular retention flange 35 and generally annular groove 37 which engage the mounting flange 39 on the container wall 36. Umbrella portion 26 is normally seated against fluid-restraining member 36 to prevent fluid from flowing through passageway 38. As shown in FIG. 6, when the fluid pressure in the upward direction exceeds a predetermined amount, umbrella portion 26 will flex to permit fluid to flow upward around the periphery of the umbrella 26. The fluid being checked and released by flexible umbrella portion 26 may, but need not be, the same as the fluid passing through flow path 16. In accordance with one aspect of the present invention, umbrella portion 26 checks and releases air to compensate for fluid transferred through flow path 16 and inverted bi-directional valve portion 18.

With the above-described construction the slit 24 will normally be closed, as seen in FIG. 1 of the drawings. As a pressure differential across the inverted bi-directional valve portion 18 increases above some preselected value, the inverted bi-directional valve portion 18 flexes in response to the pressure differential, eventually causing the slit 24 to open as seen in FIG. 2 of the drawings. The open slit 24 allows forward flow through the valve 10 in the direction indicated by the arrow 16 in FIG. 3 of the drawings. Delivery of fluid from a container causes a vacuum inside the container that will cause the umbrella portion 26 to lift up peripherally thereby allowing incoming air through fluid passageways 38 to enter the container and replace the fluid transferred from the container through flow path 16 in valve 10. Flow continues until the differential pressure is reduced sufficiently to permit slit 24 to close and the inverted bi-directional valve portion 18 returns to the normal closed configuration and the umbrella portion 26 returns to its normal position sealing the fluid passageways 38. Accordingly, fluid flow is checked through both the inverted bidirectional valve portion 18 and the umbrella portion 26 of the combination valve 10.

While the material of which the valves are constructed can affect to a great extent the pressures at which the inverted bi-directional and umbrella valves will open for flow and prevent reverse flow, the thickness and shape of the valve components can also influence the operating pressures. Adjusting the thickness of the inverted bidirectional valve portion 18 changes the amount of pressure required to open slit 24. Likewise, the amount of pressure required to flex umbrella portion 26 and open passageways 38 is dependent upon the thickness of umbrella portion 26 as well as other factors.

Figure 7:
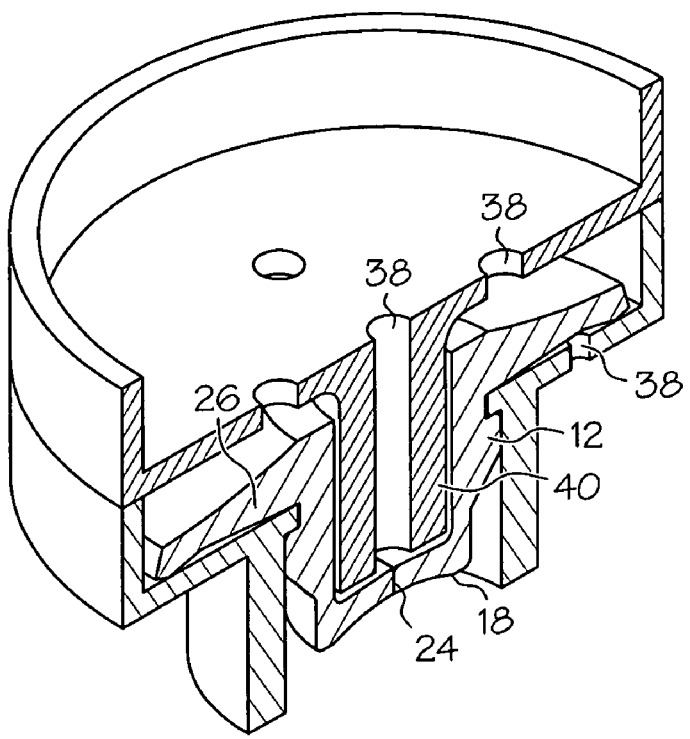
FIG. 7 is a cross-sectional view of another aspect of the invention wherein a support means is provided to prevent reverse flow through the inverted bi-directional valve portion.

In accordance with one aspect of the present invention, the combination valve 10 is provided with a means 40 for supporting the interior surface 20 of the inverted bi-directional valve 18 to prevent reverse flow (opposite flow path 16) through the slit 24. As illustrated in FIG. 7, one means 40 for supporting the interior surface 20 of the inverted bi-directional valve 18 comprises a substantially cylindrical tube 42 disposed in the valve body 12 adjacent the interior surface 20 of the inverted bi-directional valve 18. The cylindrical tube 42 can be made of any material capable of providing the necessary support to prevent reverse flow through the slit 24, but typically will be made of materials such as metals or plastics. The means for supporting the interior surface 20 of the inverted bidirectional valve 18 can be a separate structure or an integral part of the combination valve 10. In accordance with another embodiment, the means for supporting the interior surface 20 of the inverted bi-directional valve 18 can be a press-fit structure which is securely disposed in the cylindrical portion 14 of the valve body 12. Furthermore, the means could be an integral part of the valve body 12.

The combination valve 10 of the present invention can be produced in accordance with conventional molding techniques. The combination valve 10 will typically be made of a moldable elastomeric material. Elastomers useful in accordance with the present invention are not particularly limited but should be of the appropriate modulus. The material should be resilient to allow the valve to return to the normal closed position when pressure is reduced. In accordance with certain embodiments, the combination valve 10 or individual components of the valve may be constructed of one or more elastomeric compounds selected from the group consisting of nitrile rubber, hydrogenated nitrile rubber, butyl rubber, styrene-butadiene rubber, natural rubber, polyisoprene, silicone, fluorosilicone elastomers, fluorocarbon elastomers, ethylene propylene, ethylene-propylene-diene polymers (EPDM) and combinations thereof. In accordance with certain embodiments of the present invention, the combination valve 10 is of unitary construction. However, it is not beyond the scope of the present invention to produce the valve 10 from a plurality of individual components having varying compositions.

Figure 8:
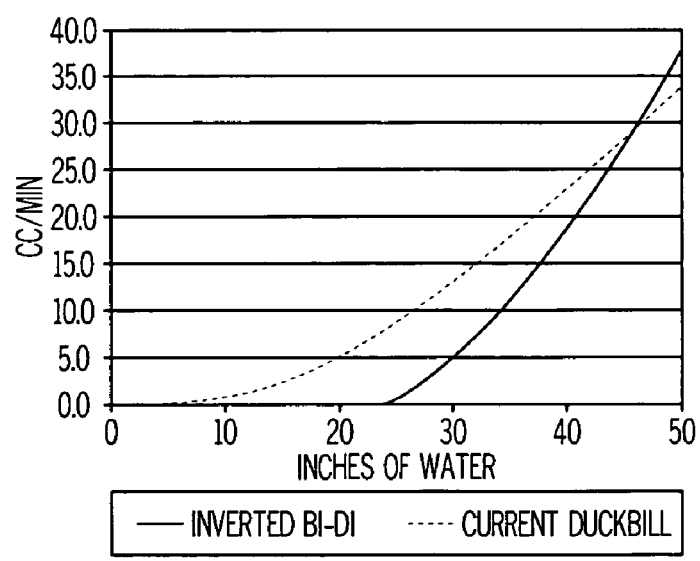
FIG. 8 is a graph illustrating the delay in flow obtained with an inverted bi-directional valve portion of a combination valve in accordance with one aspect of the present invention as compared with a duckbill portion of a conventional duckbill-umbrella combination valve.

The combination valve described in this invention may be used in a variety of fluid transfer devices such as in a liquid product dispenser, simple pump or in other fields where it is desired to permit flow of fluid in one direction, but to prevent it from flowing in the opposite direction and where a flow or relief action in the opposite direction must be provided. The combination valve of the present invention is not particularly limited to any specific dimensions or operating conditions but can be manufactured to function properly under a wide variety of operating parameters. However, typical operating pressure differentials across the inverted bi-directional valve portion 18 may be about 40 to 100 inches of water for opening the normally closed slit 24 for fluid flow in the direction of flow path 16 and a flow pressure differential of about 25 inches of water for flexing the umbrella portion 26 for fluid flow through fluid passageways 38. As shown in FIG. 8, onset of fluid flow begins at approximately 24 inches $H_2O$ for the inverted bi-directional portion of a specific combination valve in accordance with the invention compared to about 4 inches $H_2O$ for a duckbill type valve. The delay in fluid flow corresponds to less leakage and dripping through the valve.

A valve 10 of the present invention may be installed in a vessel such as a squeeze bottle (not shown) containing a liquid substance. To operate the bottle, the user squeezes the bottle, thereby increasing the pressure within the interior and the pressure of the liquid against the inverted bi-directional valve portion 18. When this pressure reaches a predetermined level, the slit 24 opens as the inverted bi-directional valve portion 18 flexes, permitting the liquid to pass through the open slit 24 and into the ambient. As the user releases the bottle, the inherent resiliency of the bottle urges it to expand and resume its original shape thereby lowering the pressure of the interior below ambient. When the ambient pressure is sufficiently above the interior pressure, the umbrella portion 26 flexes to permit air to enter the bottle through passageways 38.

Once the bottle has resumed its original, unsqueezed shape, and the interior pressure is sufficiently reduced, airflow ceases and the slit 24 closes and air flow through passageways 38 ceases. The bottle is preferably used in an inverted position so that the liquid contents bear upon the inverted bidirectional valve portion 18. Thus, when the bottle is squeezed, only liquid passes through the valve 10, instead of part liquid and part air. In such a configuration, the inverted bi-directional valve 18 prevents flow from the bottle until the user squeezes the bottle.

In accordance with another aspect of the invention, the valve may be used in an operation that requires the fluid to be drawn out under vacuum or other means of subjecting the valve to a pressure differential.

From the above it will be seen that the present invention provides a combination valve comprising an inverted bi-directional valve portion and an umbrella portion that provides increased delay prior to the onset of fluid flow in a single elastomeric part.

While the forms of apparatus herein described constitute particular embodiments of the invention, it is to be understood that the invention is not limited to these precise forms of apparatus, and that changes may be made therein without departing from the scope of the invention.

What is claimed is:

1. A combination valve comprising:

a substantially cylindrical valve body having a central longitudinal axis and defining a flow path through said valve, a resilient umbrella portion extending annularly from the valve body and the valve body terminating at an end thereof in a slit valve portion;

the slit valve portion having a curved contour about an axis of curvature extending substantially perpendicularly to and intersecting said central longitudinal axis;

said slit valve portion having a linear contour perpendicular to said central longitudinal axis such that the slit valve portion is radially asymmetrical about the central longitudinal axis;

at least one normally closed slit formed in the slit valve portion;

the slit valve portion including an exterior surface having a generally concave curved orientation when the slit is closed; and the valve body, umbrella portion and slit valve portions being formed of elastomeric material such that the slit opens to permit flow through the slit valve portion in a first direction at or above a first predetermined pressure level and said umbrella valve portion flexibly responds to a second predetermined pressure level to permit flow in a second direction.

2. The combination valve of claim 1 wherein the first direction is along the flow path from the valve body through the slit and the second direction is generally opposite the first direction wherein flow in the second direction is from under the umbrella valve portion to around the periphery thereof.

3. The combination valve of claim 1 wherein the linear contour lies in a plane which is normal to a second plane containing the curved contour.

4. The combination valve of claim 3 wherein the slit extends along the linear contour.

5. The combination valve of claim 4 wherein the slit intersects the central longitudinal axis.

6. The combination valve of claim 5 wherein the slit is radially symmetric with respect to the central longitudinal axis.

7. The combination valve of claim 6 wherein the curved contour has a substantially constant radius of curvature from the axis of curvature.

8. The combination valve of claim 7 wherein the valve body further comprises a generally annular retention flange.

9. The combination valve of claim 1 further comprising means for supporting the interior surface of the slit valve.

10. The combination valve of claim 9 wherein said means comprises a substantially cylindrical tube disposed in said valve body adjacent the interior surface of the slit valve.

11. The combination valve of claim 10 wherein said cylindrical tube is press fit in said valve body.

12. The combination valve of claim 1 wherein said valve is formed in a unitary molded construction.

13. The combination valve of claim 12 wherein said valve is constructed of an elastomeric material selected from the group consisting of nitrile rubber, hydrogenated nitrile rubber, butyl rubber, styrene-butadiene rubber, natural rubber, polyisoprene, silicone, fluorosilicone elastomers, fluorocarbon elastomers, ethylene propylene, ethylene-propylene-diene polymers (EPDM) and combinations thereof.

* * * * *